US008431545B2

(12) United States Patent
Kataoka et al.

(10) Patent No.: US 8,431,545 B2
(45) Date of Patent: Apr. 30, 2013

(54) COPOLYMER INCLUDING UNCHARGED HYDROPHILIC BLOCK AND CATIONIC POLYAMINO ACID BLOCK HAVING HYDROPHOBIC GROUP IN PART OF SIDE CHAINS, AND USE THEREOF

(75) Inventors: Kazunori Kataoka, Tokyo (JP); Nobuhiro Nishiyama, Tokyo (JP); Atsushi Ishii, Tokyo (JP); Yasuki Kato, Kashiwa (JP); Kanjiro Miyata, Tokyo (JP); Hyunjin Kim, Tokyo (JP); Hiroyasu Takemoto, Tokyo (JP)

(73) Assignee: The University of Tokyo, Tokyo (JP)

( * ) Notice: Subject to any disclaimer, the term of this patent is extended or adjusted under 35 U.S.C. 154(b) by 195 days.

(21) Appl. No.: 12/922,116

(22) PCT Filed: Mar. 6, 2009

(86) PCT No.: PCT/JP2009/054824
§ 371 (c)(1),
(2), (4) Date: Sep. 10, 2010

(87) PCT Pub. No.: WO2009/113645
PCT Pub. Date: Sep. 17, 2009

(65) Prior Publication Data
US 2011/0052917 A1 Mar. 3, 2011

(30) Foreign Application Priority Data
Mar. 10, 2008 (JP) ................................. 2008-059886

(51) Int. Cl.
*A61K 48/00* (2006.01)
*A61K 38/00* (2006.01)
*A61K 47/00* (2006.01)
*A61K 9/127* (2006.01)
*A61K 9/14* (2006.01)
*A61P 35/00* (2006.01)
*A01N 25/00* (2006.01)

(52) U.S. Cl.
USPC ......... 514/44 R; 514/1.2; 514/19.3; 514/773; 424/450; 424/486; 977/907

(58) Field of Classification Search .................... None
See application file for complete search history.

(56) References Cited

U.S. PATENT DOCUMENTS
6,576,254 B1 * 6/2003 Uchegbu ....................... 424/450

FOREIGN PATENT DOCUMENTS
| EP | 0 721 776 A1 | 7/1996 |
| EP | 1 230 934 A1 | 8/2002 |
| EP | 1 621 569 A1 | 2/2006 |
| EP | 1 859 812 A1 | 11/2007 |
| EP | 1 932 870 A1 | 6/2008 |
| EP | 2 077 293 A1 | 7/2009 |
| JP | 8-188541 | 7/1996 |
| JP | 2001-146556 | 5/2001 |
| WO | WO 99/61512 | 12/1999 |
| WO | WO 2004/105799 A1 | 12/2004 |
| WO | WO 2006/090924 A1 | 8/2006 |
| WO | WO 2007/043486 A1 | 4/2007 |
| WO | WO 2008/047948 A1 | 4/2008 |

OTHER PUBLICATIONS

Miyata, et al. (2004) "Block Cationic Polyplexes with Regulated Densites of Charge and Disulfide Cross-Linking Directed to Enhance Gene Expression", Journal of the American Chemical Society, 126(8): 2355-61.*
Dash, et al. (Oct. 13, 1997) "Synthetic polymers for vectorial delivery of DNA: characteri[z]ation of polymer-DNA complexes by photon correlation spectroscopy and stability to nuclease degradation and disruption by polyanions in vitro", Journal of Controlled Release, 48(2-3), 269-76.*
Nakanishi, et al. (2001) "Development of the polymer micelle carrier system for doxorubicin", Journal of Controlled Release, 74: 295-302.*
International Search Report, dated Jun. 16, 2009, corresponding to PCT/JP2009/054824.
Novina, et al., "The RNAi revolution," Nature, vol. 430, Jul. 8, 2004, pp. 161-164.
Pan, et al., "Antisense Applications for Biological Control," Journal of Cellular Biochemistry, vol. 98, 2006, pp. 14-35.
Crystal, "Transfer of Genes to Humans: Early Lessons and Obstacles to Success," Science, vol. 27, Oct. 20, 1995, pp. 404-410.
Tripathy, et al., "Immune response to transgene-encoded proteins limit the stability of gene expression after injection of replication-defective adenovirus vectors," Nature Medicine, vol. 2, No. 5, May 1996, pp. 545-550.
de Fougerolles, et al., "Interfering with disease: a progress report on siRNA-based therapeutics," Nature Review Drug Discovery, vol. 6, Jun. 2007, pp. 443-453.
Akhtar, et al., "Nonviral delivery of synthetic siRNAs in vivo," The Journal of Clinical Investigation, vol. 117, No. 12, Dec. 2007, pp. 3623-3632.

(Continued)

Primary Examiner — Robert M Kelly
(74) Attorney, Agent, or Firm — Christie, Parker & Hale, LLP (57) ABSTRACT

The present invention relates to a block copolymer containing an uncharged hydrophilic polymer chain block and a cationic polyamino acid chain block, wherein the hydrophilic polymer chain block is covalently bound to one end of the main chain of the polyamino acid chain block, and the hydrophobic group is covalently bound to the side chains of not less than 10% and not greater than 70% of amino acid repeating units in the polyamino acid chain block. This block copolymer forms a stable aggregate with siRNA, a small-molecule nucleic acid, under a physiological condition.

11 Claims, 7 Drawing Sheets

OTHER PUBLICATIONS

Schiffelers, et al., "Cancer siRNA therapy by tumor selective delivery with ligand-targeted sterically stabilized nanoparticle," Nucleic Acids Research, vol. 32, No. 19, Nov. 1, 2004, e149, 10 pages.

Hu-Lieskovan, et al., "Sequence-Specific Knockdown of EWS-FLI1 by Targeted, Nonviral Delivery of Small Interfering RNA Inhibits Tumor Growth in a Murine Model of Metastatic Ewing's Sarcoma," Cancer Res, vol. 65, No. 19, Oct. 1, 2005, pp. 8984-8992.

de Wolf, et al., "Effect of cationic carriers on the pharmacokinetics and tumor localization of nucleic acids after intravenous administration," International Journal of Pharmaceutics, vol. 331, 2007, pp. 167-175.

Heidel, et al., "Administration in non-human primates of escalating intravenous doses of targeted nanoparticles containing ribonucleotide reductase subunit M2 siRNA," Proceedings of the National Academy of Sciences, vol. 104, No. 14, Apr. 3, 2007, pp. 5715-5721.

Wang, et al., "The self-assembly of biodegradable cationic polymer micelles as vectors for gene transfection," Biomaterials, vol. 28, 2007, pp. 5358-5368.

Walter, et al., "Microencapsulation of DNA using poly(DL-lactide-co-glycolide): stability issues and release characteristics," Journal of Controlled Release, vol. 61, 1999, pp. 361-374.

Nicolazzi, et al., "Anionic polyethyleneglycol lipids added to cationic lipoplexes increase their plasmatic circulation time," Journal of Controlled Release, vol. 88, 2003, pp. 429-443.

Thompson, et al., "Neutral Postgrafted Colloidal Particles for Gene Delivery," Bioconjugate Chem. vol. 16, 2005, pp. 608-614.

Oupicky, et al., "Triggered intracellular activation of disulfide crosslinked polyelectrolyte gene delivery complexes with extended systemic circulation in vivo," Gene Therapy, vol. 8, 2001, pp. 713-724.

Takakura, et al., "Pharmacokinetics of succinylated proteins and dextran sulfate in mice: Implications for hepatic targeting of protein drugs by direct succinylation via scavenger receptors," International Journal of Pharmaceutics, vol. 105, 1994, pp. 19-29.

Yamasaki, et al., "Pharmacokinetic Analysis of in Vivo Disposition of Succinylated Proteins Targeted to Liver Nonparenchymal Cells via Scavenger Receptors: Importance of Molecular Size and Negative Charge Density for in Vivo Recognition by Receptors," The Journal of Pharmacology and Experimental Therapeutics, vol. 301, No. 2, 2002, pp. 467-477.

Extended European Search Report for corresponding European Patent Application No. 09720268.3, dated Dec. 27, 2011, 8pp.

* cited by examiner

COPOLYMER INCLUDING UNCHARGED HYDROPHILIC BLOCK AND CATIONIC POLYAMINO ACID BLOCK HAVING HYDROPHOBIC GROUP IN PART OF SIDE CHAINS, AND USE THEREOF

CROSS-REFERENCE TO RELATED APPLICATION

This application is a National Phase Patent Application and claims the priority of International Application Number PCT/JP2009/054824, filed on Mar. 6, 2009, which claims priority of Japanese Patent Application Number 2008-059886, filed on Mar. 10, 2008.

INCORPORATION BY REFERENCE

The material in the text file entitled "12922116SEQLIST-ING", amended Oct. 28, 2010 and being 747 bytes, is herein incorporated by reference in its entirety.

FIELD OF THE INVENTION

The present invention relates to a block copolymer containing a hydrophilic polymer chain block and a cationic polyamino acid chain block having a hydrophobic group incorporated into part of the side chains, as well as a complex of the copolymer and a nucleic acid molecule, specifically in the form of micellar particles.

BACKGROUND OF THE INVENTION

Bioactive nucleic acid pharmaceuticals including small interfering RNA (siRNA) and antisense nucleotides are expected to be next-generation drugs for treating, e.g., cancers and viral diseases. However, practical application of nucleic acids has been limited at present, since such nucleic acids are essentially unstable in vivo and have low bioavailability. In order to apply nucleic acid pharmaceuticals to treatment of a wider range of diseases, an efficient and safe nucleic acid delivery system that enables systemic administration is required (see Non-Patent Documents 1 and 2 below). Viral vectors are known to be able to deliver nucleic acids to target sites at high efficiency, but their clinical uses are limited due to, e.g., possible immunogenicity and carcinogenicity (see Non-Patent Documents 3 and 4 below). Therefore, nonviral vectors composed of cationic polymers and/or cationic lipids are attracting attention (see Non-patent documents 5 and 6 below).

Although a cationic polymer forms a complex with a nucleic acid via electrostatic interaction, such complexes are unsatisfactory in particle size control and stability in blood for the purpose of efficient delivery to targets. To address this problem, a method has been proposed which uses a cationic polymer bound to a water-soluble polymer having high biological affinity such as polyethylene glycol (PEG) (see Patent Documents 1, 2, 3, 7, and 8 below). The resultant complexes become core-shell particles having a hydrophilic shell of PEG and a core bound to a nucleic acid, thereby enabling control of particle diameter. However, it has been reported that these complexes are quickly eliminated from blood immediately after intravenous administration (see Non-Patent Documents 9 and 10 below), so that further stabilization is desired.

In brief, Patent Document 1 describes a block copolymer having a hydrophilic segment and a charged segment, as a carrier for targeted delivery of DNA, which is a charged molecule. However, a nucleic acid complex formed from this copolymer may exhibit insufficient stability in blood, as described above. Patent Document 2 is intended to address such a problem, i.e., to specifically stabilize a polymeric micelle formed of a plurality of such block copolymer molecules in an aqueous medium, by introducing mercapto groups into the charged segment of the block copolymer so that disulfide bonds is formed in the polymer molecules. Patent Document 3 provides a graft polymer in which a PEG chain (hydrophilic group) and a palmitoyl group (hydrophobic group) are bound to poly-L-lysine via ε-amino groups of the side chains.

On the other hand, another method for stabilizing a polymer micelle has been proposed, which includes preparing a cationic polymer, one end of which is bound to a PEG chain (e.g., PEGylated poly(N-methyldiethanamine sebacate), and grafting cholesterol (hydrophobic group) as a side chain to the PEGylated cationic polymer (see Non-Patent Document 11 below). Although this reference does not report on the evaluation of blood retention, it is believed that introduction of a hydrophobic group results in stabilization of the particles to a certain extent. However, preparation of this polymer requires harsh conditions (120° C., 24 hours), which may cause decomposition of the polymer, and thus it is thought to be difficult to stably control the molecular weight of the polymer and the introduction rates of PEG and cholesterol. This method also requires preparing a complex at an acidic condition of pH 4.6, which makes DNA unstable (see Non-Patent Document 12 below). These problems prevent the use of this polymer in pharmaceutical formulations. Furthermore, this reference teaches that PEG having a molecular weight of 2000 at maximum should be used at a concentration of from 1.8% to 8.2% with respect to the polymer, but such conditions will prevent sufficient formation of a hydrophilic shell. In fact, the particle diameter of the complex with DNA is as large as 200 nm or greater, and the zeta potential of the particle exhibits a negative or positive value reflecting the properties of the core. Such properties will be an obstacle to achieving high blood retention (see Non-Patent Documents 6 and 13 to 17 below, which also include other information regarding the field of the invention).

LIST OF REFERENCES

Patent Document 1: JP-H08-188541-A2
Patent Document 2: JP-2001-14556-A2
Patent Document 3: WO 99/61512
Non-Patent Document 1: C. D. Novina, et al., Nature, 2004, 430:161-164
Non-Patent Document 2: W. Pun, et al., Journal of Cellular Biochemistry, 2006, 98:14-35
Non-Patent Document 3: R. G. Crystal, et al., Science, 1995, 270:404-410
Non-Patent Document 4: S. K. Tripathy, et al., Nature Medicine, 1996, 2:545-550
Non-Patent Document 5: A. de Fougerolles, et al., Nature Review Drug Discovery, 2007, 6:443-453
Non-Patent Document 6: S. Akhtar, et al., Journal of Clinical Investigation, 2007, 117:3623-3632
Non-Patent Document 7: R. M. Schiffelers, et al., Nucleic Acids Research, 2004, 32:e149
Non-Patent Document 8: S. Hu-Lieskovan, et al., Cancer Research, 2005, 65:8984-8992
Non-Patent Document 9: H. K. de Wolf, et al., International Journal of Pharmaceutics, 2007, 331:167-175
Non-Patent Document 10: J. D. Heidel et al., Proceedings of the National Academy of Sciences, 2007, 104:5715-5721

Non-Patent Document 11: Y. Wang, et al., Biomaterials, 2007, 28:5358-5368

Non-Patent Document 12: E. Walter, et al., Journal of Controlled Release, 1999, 61:361-374

Non-Patent Document 13: C. Nicolazzi, et al., Journal of Controlled Release, 2003, 88:429-443

Non-Patent Document 14: B. Thompson, et al., Bioconjugate Chemistry, 2005, 16:608-614

Non-Patent Document 15: D. Oupicky, et al., Gene Therapy, 2001, 8:713-724

Non-Patent Document 16: Y. Takakura, et al., International Journal of Pharmaceutics, 1994, 105:19-29

Non-Patent Document 17: Y. Yamasaki, et al., Journal of Pharmacology and Experimental Therapeutics, 2002, 301: 467-477

DISCLOSURE OF THE INVENTION

As described above, research and development are being carried out on nonviral vectors for nucleic acids from various perspectives. However, there still remains a need for vectors or carriers that can efficiently deliver nucleic acids to the target. For example, although Non-Patent Document 11 discloses that micellar particles prepared from PEGylated poly (N-methyldiethanamine sebacate)-co-((cholesteryloxocarbonylamidoethyl)methylbis(ethylene)ammonium bromide sebacate)) have a certain stability, further improvement is desired from the viewpoint of providing a system capable of easily establishing the homogeneity of a pharmaceutical drug per se.

Some of the present inventors have demonstrated that, as described in above Patent Document 2, the stability of polymer micelles (or micellar particles) formed from a block copolymer can be dramatically enhanced by forming a disulfide crosslinking (covalent bonding) between the copolymer molecules. In order to increase the diversity of usable materials, however, the present inventors have been exploring other materials suitable for nucleic acid delivery.

As a result, it was found that although essentially different in structure from the copolymer described in Non-Patent Document 11, the block copolymer described in Patent Document 2, which contains an uncharged hydrophilic polymer chain block and a cationic polyamino acid chain block, can advantageously be modified by introducing a hydrophobic group into some part of the polyamino acid repeating units to thereby offer advantages to polymer micelles, compared to the case where the polymer main chains of the block copolymer molecules mentioned above were cross-linked by disulfide bonding.

Thus, the present invention provides a block copolymer containing an uncharged hydrophilic polymer chain block and a cationic polyamino acid chain block, wherein the hydrophilic polymer chain block is covalently bound to one end of the main chain of the polyamino acid chain block, and the hydrophobic group is covalently bound to the side chains of not less than 10% and not greater than 70% of amino acid units in the polyamino acid chain block.

The present invention also provides a complex of the aforementioned copolymer with a nucleic acid.

BEST MODE FOR CARRYING OUT THE INVENTION

Technical terms used in the context of the present invention should be understood as having meanings commonly used in the technical field to which the present invention pertains, unless otherwise specified.

The uncharged hydrophilic polymer chain block may be derived from a water-soluble polymer such as polyethylene glycol (or poly(oxyethylene)). The polyamino acid chain block may be derived from polymers selected from the group consisting of polylysine, polyornithine, polyarginine, polyhomoarginine and polyhistidine. The molecular weight of the uncharged hydrophilic polymer chain block is not specifically limited as long as the block copolymer can form drug-containing polymer micelles, and may be approximately 2,500 to 200,000 Da, preferably 5,000 to 20,000 Da, and more preferably 8,000 to 15,000 Da, and the number of oxyethylene repeating units may be an integer from 55 to 4,500, preferably 110 to 450, and more preferably 180 to 340.

The polyamino acid chain block, the other block of the block copolymer, may contain or consist of repeating units derived from a polymer selected from the group consisting of polylysine, polyornithine, polyarginine, polyhomoarginine and polyhistidine. The number of repeating units in this block may be an integer from 10 to 100, preferably 20 to 80, and more preferably 20 to 60. Amino acid residues of this polyamino acid chain block corresponding to 10% to 70% of the total number (an integer represented by n) of the repeating units bear hydrophobic groups in the side chains thereof. The amino acid residues bearing a hydrophobic group may be arranged in any positions in the polyamino acid block: they may be arranged at random, or may be arranged as a block (in the latter case, the polyamino acid chain block form a triblock composed of a polyethylene glycol block, a block of a polyamino acid bearing a hydrophobic group, and a block of a polyamino acid bearing no hydrophobic groups). Examples of hydrophobic groups include a residue of a sterol derivative or a $C_{4-24}$ hydrocarbyl group. The term "sterols" means natural, semisynthetic, or synthetic compounds based on a cyclopentanone hydrophenanthrene ring ($C_{17}H_{28}$). Examples of natural sterols include, but not limited to, cholesterol, cholestanol, dihydrocholesterol, cholic acid. Hemisynthetic or synthetic compounds thereof may be, e.g., synthetic precursors of these natural compounds (including, when present, compounds in which part or all of the hydroxy groups are protected with hydroxy protecting groups known to the art, or in which the carboxyl groups are protected with carboxyl protecting groups as needed). The term "sterol derivatives" means compounds based on a cyclopentanone hydrophenanthrene ring in which a $C_{1-12}$ alkyl group or a halogen atom such as chlorine, bromine or fluorine is incorporated, and which ring system may be saturated or partially saturated, as long as they have adverse effects in view of the objective of the invention. The term "residues of sterol derivatives" means groups derived by removing a hydrogen atom of the hydroxy group at position 3 of cholesterol, cholestanol, or dihydroxycholesterol structure. More preferably, they are groups derived by removing a hydrogen atom of the hydroxy group at position 3 of cholesterol. The term "hydrocarbyl" referred to in the $C_{4-24}$ hydrocarbyl group means groups composed of carbon and hydrogen atoms including: linear or branched $C_{4-24}$, preferably $C_{12-24}$ alkyls; linear or branched $C_{4-24}$, preferably $C_{12-24}$ alkenyls; linear or branched $C_{4-24}$, preferably $C_{12-24}$ alkynyls; $C_{4-24}$, preferably $C_{12-24}$ cage compounds such as adamantyls; and arylalkyls in which the aryl is phenyl or naphthyl and the alkyl is $C_1$-$C_5$, such as a benzyl group. Preferable examples include: linear or branched $C_{4-20}$, more preferably $C_{12-20}$ alkyls; linear or branched $C_{4-20}$, preferably $C_{12-20}$ alkenyls; and a benzyl group. The aforementione alkenyl and alkynyl groups may contain more than one unsaturated bond.

As more specific examples of the block copolymer, there can be mentioned a copolymer represented by general formula I or II:

In the above formulae,

A represents a hydrogen atom or a group represented by a formula $R_1(R_2)CH(CH_2)_q$— wherein $R_1$ and $R_2$ independently represent a hydrogen atom, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkylsiloxy group, a siloxy group, or a silylamino group, or $R_1$ and $R_2$ together form an ethylenedioxy or propylenedioxy group which is unsubstituted or substituted with a $C_{1-3}$ alkyl group, or $R_1$ and $R_2$, together with the =CH— group to which they are attached, form a formyl group, q represents an integer of 0 to 10, L represents —$(CH_2)_r$NH—, —NHCH$_2$CH$_2$NH—, —NHCH$_2$CH$_2$CH$_2$NH—, or —COCH$_2$CH$_2$—NH— provided that r represents an integer of 0 to 5, L' represents —CO—, —OCO—$(CH_2)_{r'}$—CO—, and —NHCO—$(CH_2)_{r'}$—CO— provided that r' represents an integer of 1 to 5, B represents a sterol derivative residue or a $C_{4-24}$ hydrocarbyl group, bound via —NH—, —NHCOO—, —NHCO— or a substituent represented by formula III:

Q represents NH$_2$, —NHC(=NH)NH$_2$ or a substituent represented by formula IV:

Z represents a hydrogen atom, a $C_{2-12}$ alkylcarbonyl group, a $C_{3-12}$ alkenylcarbonyl group, a $C_{3-12}$ alkenylcarbonyl group, an arylcarbonyl group, an aryloxycarbonyl group, an aryl $C_{1-3}$ carbonyl group, or a group defined in B, Z' represents —NH—$R_3$, provided that $R_3$ is an unsubstituted or substituted, linear or branched $C_{1-12}$ alkyl group, m is an integer of 55 to 5,000, n is an integer of 10 to 100, p is an integer of 1, 3, or 4, x is an integer representing the number of units having a substituent Q contained in the polyamino acid chain block, and y is an integer representing the number of units having a substituent B contained in the polyamino acid chain block, wherein x+y=n, and y accounts for not less than 10% and not greater than 70% of n.

As the $C_{1-12}$ alkyl or $C_{1-3}$ alkyl in the above formulae, or the alkyl as used herein, there can be mentioned linear or branched alkyls each having an appropriate number of carbons, such as methyl, ethyl, propyl, iso-propyl, n-butyl, sec-butyl, tert-butyl, n-pentyl, n-hexane, n-heptanedecane, and undecyl.

Block copolymers before incorporation of a hydrophobic group, including block copolymers of the above formula in which B is a hydrogen atom, are conventional, or can be prepared by a conventional method. Generally, block copolymers for use in the present invention may be prepared by using a polymer having an uncharged hydrophilic polymer chain and a polymer having a cationic polyamino acid chain, both of which polymers may be conventional or commercially available, and coupling these polymers either without pretreatment or, if necessary, after purification so as to narrow the molecular weight distribution thereof. Introduction of a hydrophobic group into side chains of the polyamino acid may be performed either before or after preparation of a block copolymer by coupling it with an uncharged hydrophilic polymer chain. According to this method, the resultant copolymer would have a structure as defined by general formula I or II. Alternatively, a block copolymer of the present invention in which, e.g., the uncharged hydrophilic polymer chain is a polyethylene glycol chain and the polyamino acid chain is lysine or ornithine, can be prepared by another method which includes the steps of: obtaining the polyethylene glycol chain by anionic living polymerization using an initiator capable of providing group A of general formula I; introducing an amino group into the growing end thereof; polymerizing, at the amino end, a N-carboxylic anhydride (NCA) of a protected amino acid such as Nε-TFA-L-lysine, Nε-Z-L-lysine, Nδ-Z-L-ornithine, 1-benzyl-L-histidine, and Nδ, Nω-di-Z-L-arginine to synthesize a block copolymer; and introducing a hydrophobic group to side chains of the polyamino acid thereof to thereby prepare the desired block copolymer of the present invention. According to this method, the resultant copolymer has a structure as defined by general formula I. Also, simultaneously with introduction of the side chain group, as needed, a group identical to the side chain group other than the hydrogen atom may be introduced as group Z of general formula I.

In the above formula, Q represents $NH_2$, —$NHC(=NH)NH_2$, or a substituent expressed by formula III, two or more of which may be present in the same molecule:

(III)

The substituent represented by —$C(=NH)NH_2$ can be introduced into Q of the above formula by, for example, reacting 3,5-dimethyl-1-pyrazolylformaminidium nitrate to the amino group present in the side chain of lysine and ornithine residues in the block copolymer, or by reacting O-methylisourea in the presence of, e.g., ammonium hydroxide. These reactions may be performed either before or after introducing a hydrophobic group into B.

The thus-provided block copolymer of the present invention has a cationic charged group, and thereby can form an ion complex with an anionic charged compound, a nucleic acid, or an anionic charged drug. Such an ion complex can form an autonomously aggregated micelle, i.e., a so-called polymer micelle. Such a micelle may take a core-shell structure in which the core part encapsulates a nucleic acid or a drug, while the shell part contains an uncharged hydrophilic polymer chain. The micelle may also be conferred target directivity by incorporating, into the block copolymer, a ligand or antibody (a fragment thereof: such as F(ab')2 and F(ab)) that can bind to, e.g., a specific receptor protein thereto via a specific functional group represented by $R_1R_2CH$— of the block copolymer represented by General formula I such as a formyl group, amino group, or carboxyl group, optionally after, if necessary, introducing a binding group having, e.g., an active ester group or a maleimide group into the block copolymer.

Any nucleic acids or drugs that can form an ion complex mentioned above may be used without limitation as long as they can enhance stability. Nucleic acids are preferably used, so that the following explanation will be made on nucleic acids for the purpose of simplifying explanation. The term "nucleic acids" as used herein means polynucleotides or oligonucleotides having a purine or pyrimidine base, a pentose, and a phosphoric acid as a basic unit. Examples of nucleic acids include oligo or poly double-stranded RNA, oligo or poly double-stranded DNA, oligo or poly single-stranded DNA, and oligo or poly single-stranded RNA, as well as oligo or poly double-stranded or single-stranded nucleic acids containing both DNA and RNA in a single strand. Also, nucleotides contained in these nucleic acids may be naturally occurring forms or chemically-modified, non-naturally occurring forms, or may be forms in which a molecule such as an amino group, thiol group or fluorescent compound has been added. These nucleic acids may contain, but not limited to, 4 to 20,000 bases, preferably 10 to 10,000 bases, and more preferably 18 to 30 bases. In view of functions or actions, there can be mentioned plasmid DNA, siRNA, micro RNA, an antisense nucleic acid, a decoy nucleic acid, an aptamer, and a ribozyme. Any siRNA may be used as long as it was designed by a conventional method so as to interact with a target gene or a polynucleotide. The siRNA may be either a single- or double-stranded nucleotide having approximately 18 to 30 nucleotides, and encompasses all conventional compounds in the art as well as all nucleotides having actions or functions similar thereto. Specific siRNA may be designed by referring to genes subject to gene therapy.

Such genes include, but not limited to: PKCα, which is associated with, e.g., non-small cell lung cancer; BCL-2, which is associated with, e.g., malignant melanoma; ICAM-1, which is associated with Crohn's disease; HCV, which is associated with type C hepatitis; TNFα, which is associated with rheumatoid arthritis or psoriasis; the adenosine AI receptor, which is associated with asthma; the c-raf kinase, which is associated with, e.g., ovarian cancer; H-ras, which is associated with, e.g., pancreatic cancer; c-myc, which is associated with ischemic heart diseases; PKA Ria, which is associated with colon cancer; HIV, which is associated with AIDS; the DNA methyl transferase, which is associated with solid tumors; the VEGF receptor, which is associated with cancers; the ribonucleotide reducing enzyme, which is associated with renal cancer; CMV IE2, which is associated with CMV retinitis; MMP-9, which is associated with prostatic cancer; TGFβ2, which is associated with malignant glioma; CD49d, which is associated with multiple myeloma; PTP-1B, which is associated with diabetes mellitus; c-myb, which is associated with cancers; EGFR, which is associated with breast cancer; and mdr1, autotasin and GLUT-1, which are associated with cancers.

Any conventional antisense nucleic acids in the art can also be used, as well as all nucleic acids having an equivalent function or action. Such a function involves hybridization with mRNA leading to the formation of a double-stranded molecule, which then inhibits gene translation. On the other hand, ribozyme means a RNA molecule having an ability of specifically decomposing another single-stranded RNA, similarly to DNA-restriction endonuclease.

A complex of the block copolymer of the present invention and a nucleic acid can be prepared by a method which includes the steps of: dissolving the block copolymer and the nucleic acid into water containing a polar organic solvent; and lowering the content of the polar organic solvent in the resultant solution. Examples of the polar organic solvents include, but not limited to, one or more compounds selected from the group consisting of dimethyl sulfoxide, dimethyl formamide, dimethyl acetamide, methanol, ethanol, isopropanol, acetonitrile, acetone, methylethylketone, 1-propanol, 2-propanol, 1-butanol, 2-methyl-1-propanol, 2-butanol, 2-methyl-2-propanol, tetrahydrofuran, and dioxane. Examples of methods for lowering the content of the polar organic solvent-containing aqueous solution include, but not limited to, a method using dialysis or evaporation, or a method of dilution followed by, as needed, concentration using, e.g., ultrafiltration.

When forming the complex of the present invention, the block copolymer and the nucleic acid should preferably be mixed at a N/P ratio of 1 to 50, more preferably 2 to 20, and still more preferably 4 to 10, wherein the N/P ratio is defined as [molar concentration of cationic residues in the block copolymer]/[molar concentration of phosphate residues in the nucleic acid]. As used herein, the molar concentration of cationic residues in the block copolymer can be calculated as the sum of the molar number of lysine, ornithine, arginine, homoarginine, and histidine residues contained in the polyamino acid chain block in the block copolymer, as well as the molar number of, if present, the lysine and ornithine residues to which the hydrophobic group is bound to thereby form secondary amino groups, and the molar number of the histidine residue to which the hydrophobic group is bound. For example, when the block copolymer is represented by general formula I or II, the molar concentration of cation residues can be calculated as the sum of the molar number of substituents represented by $NH_2$ in Q, substituents represented by —NHC(=NH)$NH_2$, substituents represented by formula IV, hydrophobic substituents bound to the polyamino acid block via —NH— in B, and hydrophobic substituents bound to the polyamino acid block via the substituent represented by formula III in B.

The complex of a block copolymer of the present invention and a nucleic acid should preferably be in the form of particles having an average diameter of 10 to 300 nm, and more preferably, an average diameter of 20 nm to 200 nm.

The complex of a block copolymer of the present invention and a nucleic acid should preferably have a zeta potential of −10 to 10 mV, and more preferably −5 to 5 mV.

In accordance with the present invention, the complex of a block copolymer and a nucleic acid has the following characteristics and advantages:

Characteristics:

The complex can be prepared under a mild condition, allowing for stable production without unstabilizing the nucleic acid. Furthermore, since the binding with the nucleic acid is reversible, it does not change the chemical structure of the nucleic acid or damage the characteristics and activity of the nucleic acid.

Advantages:

Since the complex is easy to produce, it has excellent industrial productivity and thus provides a medical economic advantage. In addition, since the complex is highly stable in a living body and has significantly-improved bioavailability after administration by, e.g., injection, various advantages can be expected, such as reduction in medical costs due to dramatic reduction in dosage and effective expression of pharmacological effects. Dosage reduction is also beneficial from the viewpoint of reducing side effects, such as induction of immunological responses to the nucleic acid and adverse effects on the blood coagulation system due to chemically-modified oligonucleic acids.

The present invention will be explained in further detail with reference to specific examples, although it should be noted that they are presented only for the purpose of facilitating understanding of the present invention and are not intended to limit the present invention.

Example 1

Synthesis of a Polyethylene Glycol-poly(L-lysine) Block Copolymer and Introduction of Cholesterol Groups into the Polymer (1) 1.5 g of α-methoxy-ω-aminopoly(ethylene glycol) (NOF Corp.) with a Mw (weight-average molecular weight) of 12,000 was dissolved in 22.5 ml of dimethyl sulfoxide, to which 1.5 g (45 times the amount of polyethylene glycol) of N-carboxylic anhydride (NCA) of ε-trifluoroacetyl-L-lysine in 22.5 ml of dimethyl sulfoxide was added and reacted at 35° C. for 48 hours. Poly(ethylene glycol)-block-poly(ε-trifluoroacetyl-L-lysine) (PEG-P(Lys(TFA))) thus obtained was dissolved in 300 ml of methanol and 30 ml of 1N NaOH, and stirred at 35° C. for 6 hours for deprotection. The resultant solution was purified by dialyzing three times against 0.01N HCl using a regenerated cellulose dialysis tubing (Spetra/Por 1, Spectrum Laboratories) with a molecular weight cut off of 6000 to 8000. The solution in the dialysis tubing was lyophilized to obtain 2.2 g of the hydrochloride of poly(ethylene glycol)-block-poly(L-lysine) (PEG-P(Lys)). $^1$H-NMR analysis revealed that the degree of polymerization of the P(Lys) moiety was 40.

(2) Introduction of Cholesterol Groups (i)

50 mg of the hydrochloride of PEG-P(Lys) was dissolved in 2.5 ml of methanol, to which 4.8 mg (a molar fraction of 10% relative to the lysine unit) cholesteryl chloroformate in 2.5 ml of methylene chloride was added, followed by addition of 30 μl of triethylamine, and the resultant solution was stirred at room temperature for 24 hours. The reaction mixture was added dropwise to 150 ml of a diethylether solution to cause precipitation of the polymer, which was collected by filtration under reduced pressure, and dissolved into 5 ml of 0.01 N hydrochloric acid and 5 ml of methanol. The resultant solution was dialyzed twice for 2 hours each against 500 ml of 0.01 N hydrochloric acid using a dialysis membrane with a molecular weight cut off of 6000 to 8000. After replacing the solution outside the dialysis membrane with 500 ml of water, dialysis was continued for additional 2 hours, after which the solution in the dialysis membrane was lyophilized to obtain 38 mg of a white solid product of interest, i.e., the hydrochloride of PEG-PLys (cholesterol) (hereinafter referred to as PPLC1).

Figure 1:
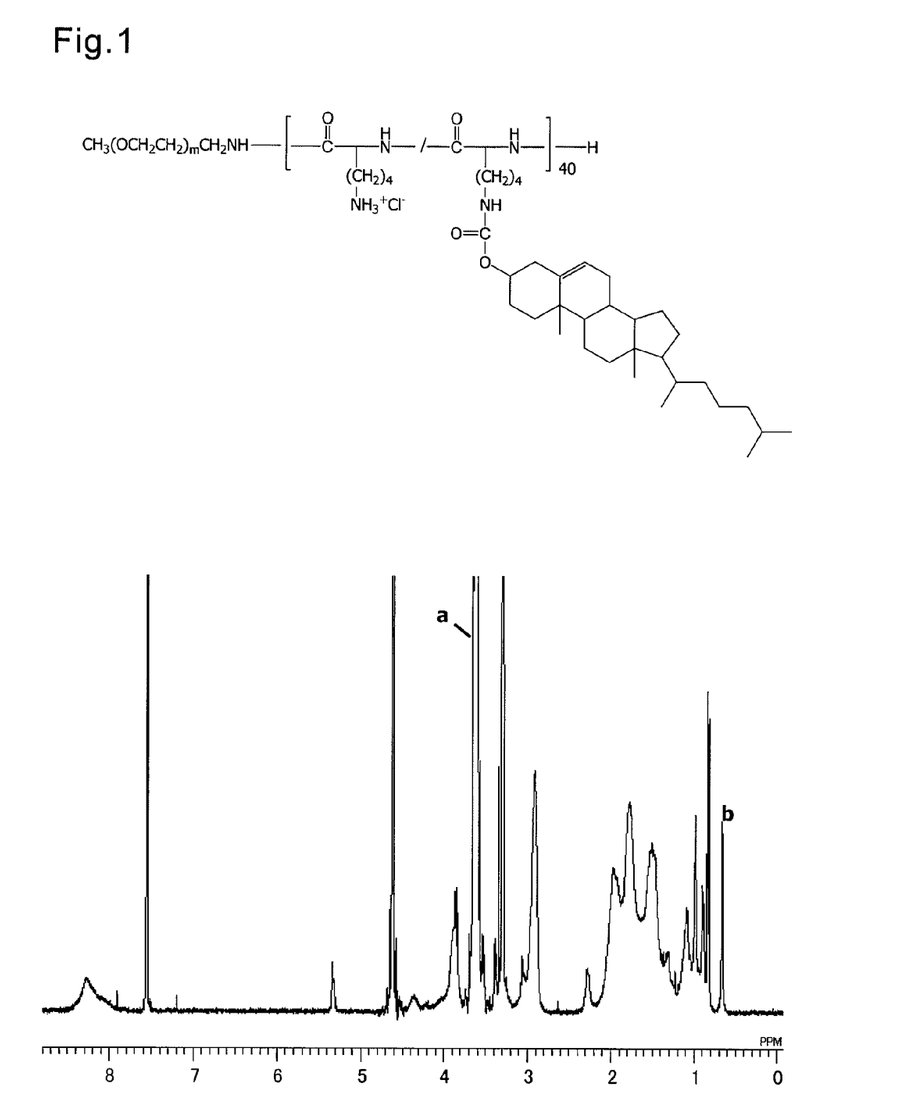
FIG. 1 is a $^1$HNMR spectrum of PPLC1 that was synthesized in Example 2. In the figure, "a" represents a peak derived from the methylene group of polyethylene glycol, and "b" represents a peak derived from the methyl group in the cholesterol group.

The structure of the polymer obtained was analyzed by ¹H-NMR (see FIG. 1 for the spectrum).

As the solvent for NMR, a mixture of methanol-d4 and chloroform-d at a volume ratio of 1:1 was used. The rate of introduction of cholesterol groups was calculated from the ratio of strength of the proton peak of methyl groups (CH$_3$: 0.6 ppm) derived from cholesterol groups to the proton peak of methylene groups (OCH$_2$CH$_2$: 3.5 ppm) of PEG. It was found that in the PPLC1 obtained in this example, cholesterol groups were introduced at 11% of the total lysine units.

Example 2

Introduction of Cholesterol Groups into the Polyethylene Glycol-poly(L-lysine) Block Copolymer (ii)

PPLC(2) to (5) were prepared according to the same method as described in Example 2 except that the amount of cholesteryl chloroformate added was changed as shown in Table 1, which also shows the molar fraction of cholesteryl chloroformate relative to the lysine units and the rate of introduction of cholesterol groups relative to the lysine units, which were obtained from ¹H-NMR analysis. PPLC5, in which cholesteryl chloroformate was added at 70% relative to the lysine units, was insoluble in the NMR solvent, so that the rate of introduction of cholesterol groups could not be calculated.

TABLE 1

| Polymer | Amount of cholesteryl formate added (mg) | Molar fraction of cholesteryl formate added relative to lysine units (%) | Rate of introduction of cholesterol groups relative to lysine units (%) |
|---|---|---|---|
| PPLC1 | 4.8 | 10 | 11 |
| PPLC2 | 12.1 | 25 | 24 |
| PPLC3 | 19.3 | 40 | 44 |
| PPLC4 | 26.6 | 55 | 56 |
| PPLC5 | 33.8 | 70 | — |

Example 3

Introduction of Stearoyl Groups into the Polyethylene Glycol-poly(L-lysine) Block Copolymer 1.87 g of stearic acid was dissolved in 50 ml of dichloromethane, to which 0.76 g of N-hydroxysuccinimide and 1.25 g of 1-ethyl-3-(3-dimethylaminopropyl)carbodiimide hydrochloride were added and stirred at room temperature for 24 hours. After the reaction, the solution was combined with 100 ml of water and subjected to liquid-liquid separation using a separatory funnel. The organic phase obtained was dehydrated with magnesium sulfate, and enriched using an evaporator. The enriched solution was added dropwise to 20 volumes of ethanol to form a white precipitate, which was collected by filtration and dried under reduced pressure to obtain N-succinimidyl stearate.

50 mg of the hydrochloride of PEG-P(Lys) was dissolved in 2.5 ml of methanol, to which 16.4 mg (a molar fraction of 40% relative to the lysine units) of N-succinimidyl stearate in 2.5 ml of methylene chloride was added, followed by addition of 37.5 μl of diisopropylethylamine, and the resultant mixture was stirred at room temperature for 24 hours. The reaction mixture was then added dropwise to 600 ml of a diethylether solution to cause precipitation of the polymer, which was collected by filtration under reduced pressure, and dissolved into 5 ml of 0.01 N hydrochloric acid and 5 ml of methanol. The solution was then dialyzed twice for 2 hours each against 500 ml of 0.01 N hydrochloric acid using a dialysis membrane with a molecular weight cut off of 6000 to 8000. After replacing the solution outside the dialysis membrane with 500 ml of water, dialysis was continued for additional 2 hours. The liquid inside the dialysis membrane was lyophilized to obtain a white solid product of interest, i.e., the hydrochloride of PEG-PLys (stearoyl) (hereinafter referred to as PPLS1).

Figure 2:
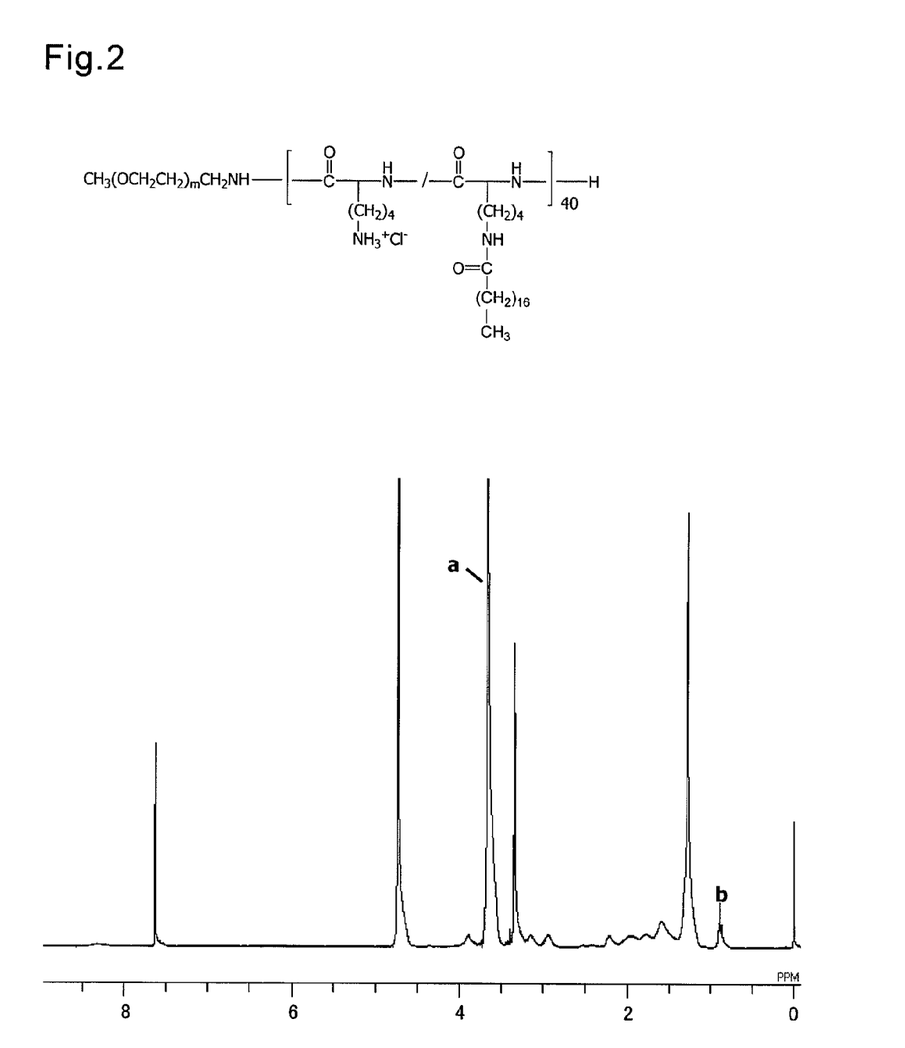
FIG. 2 is a $^1$HNMR spectrum of PPLS1 that was synthesized in Example 2. In the figure, "a" represents a peak derived from the methylene group of polyethylene glycol, and "b" represents a peak derived from the methyl group in the stearoyl group.

As in Example 1, PPLS1 was analyzed by ¹H-NMR (see FIG. 2 for the spectrum). The rate of introduction of stearoyl groups was calculated from the ratio of strength of the proton peak of the methyl groups (CH$_3$: 0.8 ppm) to the proton peak of methylene groups (OCH$_2$CH$_2$: 3.5 ppm) of PEG. It was found that in the PPLS1 obtained in this example, stearoyl groups were introduced at 40% of the total lysine units.

Example 4

Synthesis of the Polyethylene Glycol-poly(L-lysine-ε-benzyloxycarbonyl)-poly(L-lysine) Block Copolymer (1) 1.5 g of α-methoxy-ω-aminopoly(ethylene glycol) (NOF Corp.) with a Mw (weight-average molecular weight) of 12,000 was dissolved in 22.5 ml of dimethyl sulfoxide, to which 1.03 g (27 equivalents relative to polyethylene glycol) of the N-carboxylic anhydride (NCA) of ε-benzyloxycalcarbonyl-L-lysine and 603 mg (18 equivalents relative to polyethylene glycol) of the N-carboxylic anhydride (NCA) of ε-trifluoroacetyl-L-lysine dissolved in 24.5 ml of dimethyl sulfoxide were added and reacted at 35° C. for 48 hours. Poly(ethylene glycol)-block-poly(ε-benzyloxycarbonyl-L-lysine/ε-trifluoroacetyl-L-lysine) (PEG-P(Lys(Z)/Lys(TFA)) thus obtained was dissolved in 300 ml of methanol and 30 ml of 1N NaOH, and stirred at 35° C. for 6 hours for deprotection. This solution was purified by dialyzing three times against 0.01N HCl using a regenerated cellulose dialysis tubing (Spetra/Por 1, Spectrum Laboratories) with a molecular weight cut off of 6000 to 8000. The solution in the dialysis tubing was lyophilized to obtain, as a polyamino acid block, 2.0 g of the hydrochloride of poly(ethylene glycol)-block-poly(ε-benzyloxycarbonyl-L-lysine/L-lysine) (PEG-P(Lys (Z)/Lys) (hereinafter referred to as PPLZ), in which ε-benzyloxycarbonyl-L-lysine groups and L-lysine groups were polymerized at random. ¹H-NMR analysis revealed that the number of ε-benzyloxycarbonyl-L-lysine units contained in a polymer was 24, and that the number of L-lysine units contained was 16.

Example 5

Synthesis of a Polyethylene Glycol-poly(L-lysine-ε-benzyloxycarbonyl)-poly(L-lysine) Block Copolymer (1) 1.5 g of α-methoxy-ω-aminopoly(ethylene glycol) (NOF Corp.) with a Mw (weight-average molecular weight) of 12,000 was dissolved in 22.5 ml of dimethyl sulfoxide, to which 1.03 g (27 equivalents relative to polyethylene glycol) of the N-carboxylic anhydride (NCA) of ω-benzyloxycarbonyl-L-lysine dissolved in 15.5 ml of dimethyl sulfoxide was added and reacted at 35° C. for 24 hours. Then, 603 mg (18 equivalents relative to polyethylene glycol) of the N-carboxylic anhydride (NCA) of ε-trifluoroacetyl-L-lysine dissolved in 9 ml of dimethyl sulfoxide was added and reacted at 35° C.

for another 24 hours. Poly(ethylene glycol)-block-poly(ε-benzyloxycarbonyl-L-lysine)-block-poly(ε-trifluoroacetyl-L-lysine) (PEG-P(Lys(Z)-block-PLys(TFA)) thus obtained was dissolved in 300 ml of methanol and 30 ml of 1N NaOH, and stirred at 35° C. for 6 hours for deprotection. This solution was purified by dialyzing three times against 0.01N HCl using a regenerated cellulose dialysis tubing (Spetra/Por 1, Spectrum Laboratories) with a molecular weight cut off of 6000 to 8000. The solution in the dialysis tubing was lyophilized to obtain 2.0 g of the hydrochloride of poly(ethylene glycol)-block-poly(ε-benzyloxycarbonyl-L-lysine)-block-poly(L-lysine) (PEG-PLys(Z)-PLys) (hereinafter referred to as PPLZb), which was in the form of a triblock of poly(ethylene glycol), poly(ε-benzyloxycarbonyl-L-lysine), and poly(L-lysine). $^1$H-NMR analysis revealed that the degrees of polymerization of poly(ε-benzyloxycarbonyl-L-lysine) portion and poly(L-lysine) portion were 24 and 16, respectively.

Example 4

Preparation of Particles

A siRNA used in this example was designed to target the sea firefly luciferase gene. Specifically, it was synthesized into a double-stranded form through a standard method using a sense strand of 5'-CUUACGCUGAGUACUUCGAdTdT-3' and an antisense strand of 5'-UCGAAGUACUCAGCGUAAGdTdT-3'. It was synthesized by NIPPON EGT Co., Ltd., and purchased therefrom.

The siRNA was dissolved into 10 mM Tris-HCl buffer (1.0 ml), pH 7.4, so as to be in a concentration of 20 μM. 250 μl of this siRNA solution was mixed with 250 μl of the PPLC1 solution in DMF, which had been prepared in advance in such a concentration as to satisfy a desired N/P ratio, wherein the N/P ratio means [the concentration of cation residues in a block copolymer]/[the concentration of phosphate groups in a nucleic acid]. This solution was dialyzed three times each for 4 hours using a dialysis kit (Slide-A-Lyzer Dialysis Casset, Pierce) with a molecular-weight cut off of 10,000 against 50 ml of 10 mM Tris-HCl buffer at pH 7.4 to obtain a solution of particles encapsulating the siRNA. As necessary, the concentration of the particle solution was adjusted either by dilution with 10 mM Tris-HCl buffer, pH 7.4, or by enrichment using a centrifuge filtration unit (Amicon Ultra, Millipore).

Particles were similarly prepared using PPLC2 to PPLC4, PPLS1, PPLZ, PPLZb and PEG-P(Lys).

Example 5

Characterization by Electrophoresis

Each particle solution containing 100 ng of siRNA was loaded onto a polyacrylamide gel (Novex 20% TBE Gel, Invitrogen), and electrophored using a TBE solution as the electrophoresis buffer at a condition of an applied voltage of 100 V and a migration time of one hour. After the electrophoresis was completed, the gel was stained with SYBR (registered trademark) Green II (Invitrogen) and then imaged using the Molecular Imager FX (Bio-Rad).

Figure 3:
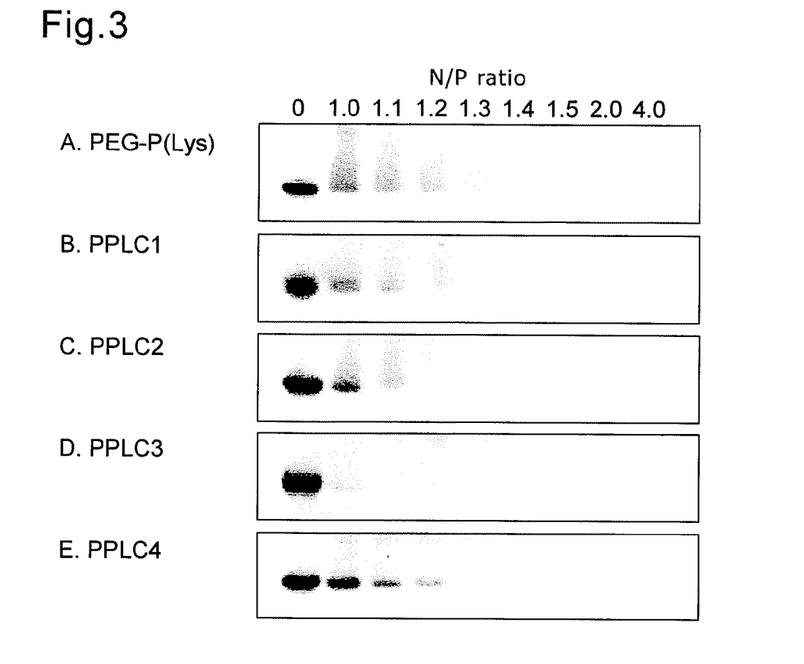
FIG. 3 is a photograph taken after electrophoresis of the solutions of particles formed using each of polymers PPLC1 to PPLC4 and PEG-P (Lys) together with siRNA at each N/P ratio (the N/P ratio of "0" indicates a lane in which siRNA alone was subjected to electrophoresis).

The result is shown in FIG. 3. If siRNA is incorporated into the particles, the degree of migration would become smaller in electrophoresis, and thus bands derived from free siRNA would disappear. For all the analyzed polymers, no bands derived from free siRNA were identified when the N/P ratio is 1.5 or greater, which results show that almost all of the siRNA added was incorporated into the particles.

Example 6

Characterization by Dynamic Light Scattering (DLS)

Each particle solution was measured for the polydispersity index (PDI) of particles, the cumulative mean particle size, and the particle diameter distribution histogram by means of a dynamic light scattering method using the Zetasizer Nano ZS (Malvern Instruments). The siRNA concentration of each particle solution was adjusted to 5 μM before measurement.

Figure 4:
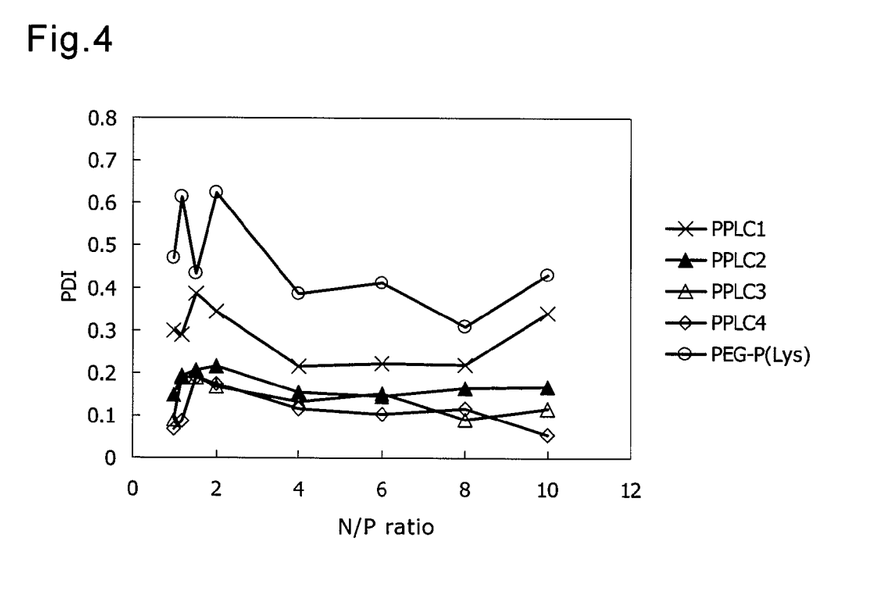
FIG. 4 is a graph showing the polydispersity index (PDI) measured by dynamic light scattering of aggregates formed using each of polymers PPLC1 to PPLC4 and PEG-P (Lys) with siRNA.
Figure 5:
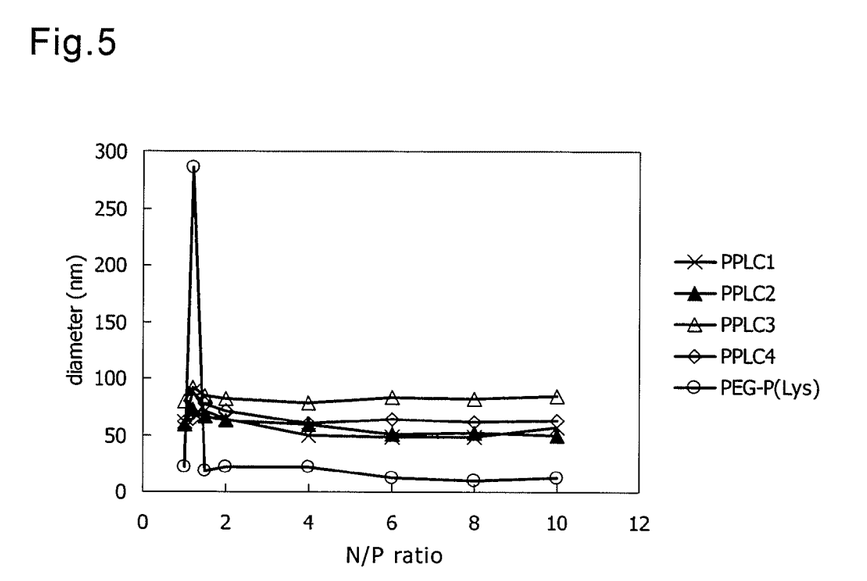
FIG. 5 is a graph showing the cumulant particle diameter measured by dynamic light scattering of aggregates formed using each of polymers PPLC1 to PPLC4 and PEG-P (Lys) with siRNA.
Figure 6:
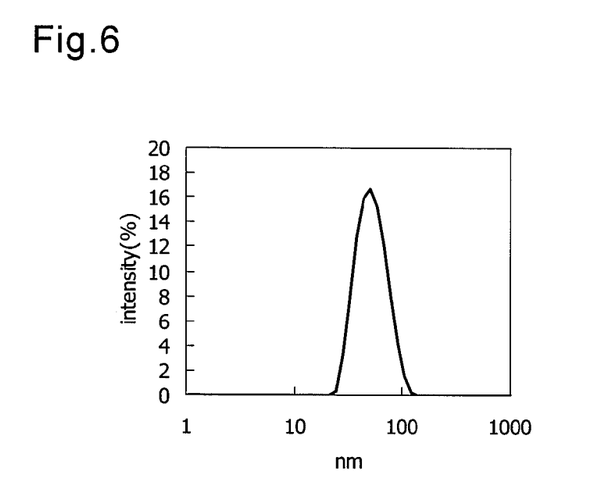
FIG. 6 is a histogram of particle size distribution measured by dynamic light scattering of particles formed using PPLC2 and siRNA at an N/P ratio of 6.

The results are shown in FIGS. 4 to 6. According to the results of FIG. 4 indicate that the particles formed using PEG-PLys free from hydrophobic groups had a large PDI, indicating that heterogeneous aggregates were formed. In contrast, the particles formed using PPLC1 to PPLC4 had smaller PDI values and narrower distributions. In particular, the particles formed using PPLC2 to PPLC4, in which 24% or more cholesterol was introduced relative to the lysine units, had PDI values of 0.25 or less, indicating that monodisperse particles were obtained.

The result of FIG. 5 indicated that for the particles formed using PPLC1 to PPLC4, the cumulative mean particle diameters were within the range of from 40 to 100 nm at any N/P ratio. As a representative example, a histogram of the particle diameter distribution of the particles formed using PPLC2 at an N/P ratio of 6 with siRNA is shown in FIG. 6.

Example 7

Characterization by Zeta Potential Measurement

Figure 7:
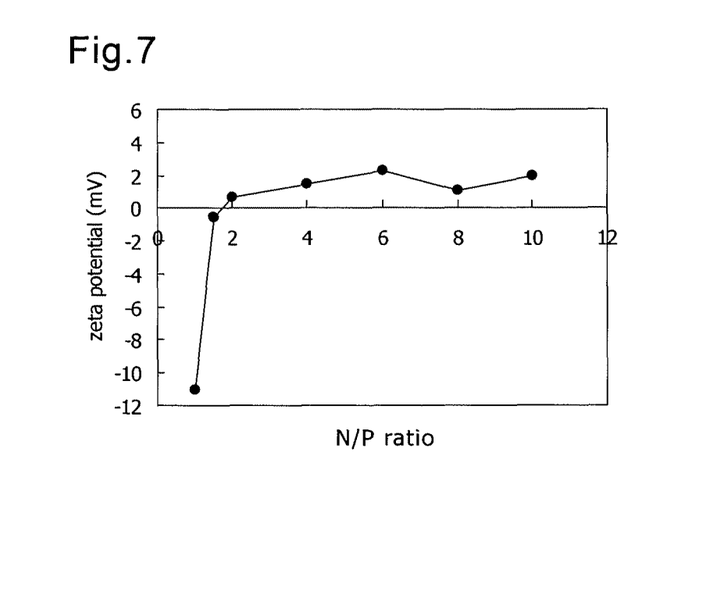
FIG. 7 is a graph showing the result of measuring the zeta potential of aggregates formed from PPLC2 and siRNA.

The particles formed using PPLC2 were measured for zeta potentials using the Zetasizer Nano ZS (Malvern Instruments), the results of which are shown in FIG. 7. The zeta potential was negative at an N/P ratio of 1, but when the N/P ratio is in the range of 1.5 to 10, the absolute value of the zeta potential was very small, being almost 0 mV. Since the zeta potential was maintained at a small value even under conditions of excessive cation charges, it can be seen that a PEG layer was formed at the surface of the particles, completely shielding the electric charge within the particles.

Example 8

Evaluation of Blood Circulation

A siRNA used in this example was designed to target the sea firefly luciferase gene and labeled with CY3 at the 5'-end of the antisense strand. Specifically, it was synthesized into a double-stranded form through a standard method using a sense strand of 5'-CUUACGCUGAGUACUUCGAdTdT-3' (SEQ ID NO: 1) and an antisense strand of 5'-Cy3-UCGAAGUACUCAGCGUAAGdTdT-3' (SEQ ID NO: 2). It was synthesized by NIPPON Bioservice, and purchased therefrom.

Solutions of particles encapsulating Cy3-lebled siRNA were prepared using each polymer in a manner similar to that described in Example 5. To these solutions, 1/20 volume of an aqueous solution of 3M sodium chloride was added to make an isotonic solution containing 150 mM sodium chloride, which was used for evaluation.

To Balb/c mice (Charles River Laboratories Japan, Inc.), a particle solution containing 20 μg of Cy3-modified siRNA was administered via a tail vein, and after a given time, 200 μl of blood was drawn through a lower aorta. The blood was then centrifuged at 4° C. and 2000 G for 10 minutes to obtain 70 μl of plasma from the supernatant. This plasma was combined with 5 μl of a ¹⁄₄₀₀ N potassium polyvinylsulfate solution (Wako Pure Chemical Industries, Ltd.), and then subjected to measurement of fluorescence intensity using the Fluoroskan Ascent FL system (Lab systems) (excitation wavelength 544 nm, emission wavelength 590 nm). From this fluorescence intensity, Cy3 remaining in blood was determined and used for evaluation of blood circulation. The residual rate in plasma relative to the amount administered was calculated assuming that the amount of blood in a mouse was 80% of the body weight.

Figure 8:
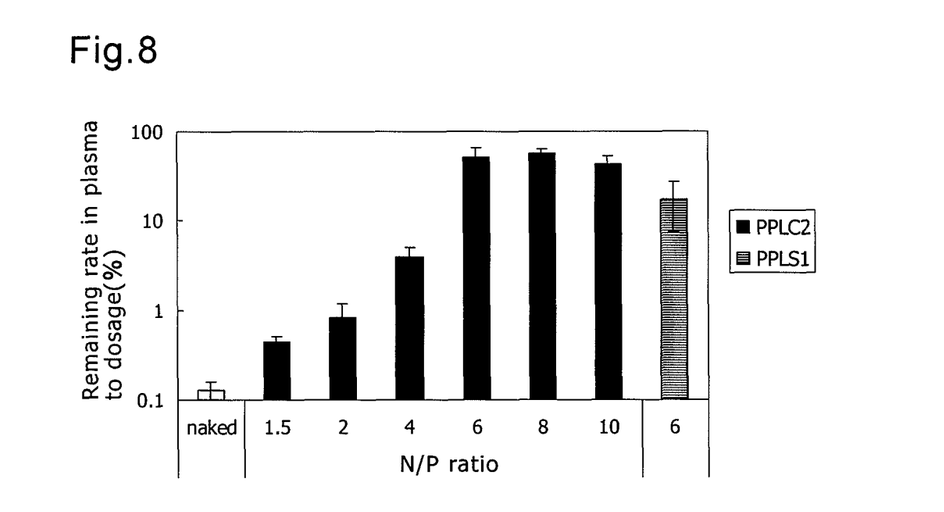
FIG. 8 is a graph showing the results of evaluating blood circulation one hour after administration of particles prepared using PPLC2 at N/P ratios of from 1.5 to 10, particles prepared using PPLS1 at an N/P ratio of 6, and non-encapsulated (naked) siRNA.

The results of evaluation of blood circulation one hour after administration of the particles prepared using PPLC2 at N/P ratios of from 1.5 to 10, particles prepared using PPLS1 at an N/P ratio of 6, and non-encapsulated (naked) siRNA are shown in Table 2 and FIG. 8. For PPLC2, the particles prepared with N/P ratios of from 6 to 10 exhibited higher blood-circulating rate as compared to the particles prepared with N/P ratios of from 1.5 to 4. Also, the particles prepared using PPLS1 with an N/P ratio of 6 exhibited a good blood-circulating rate, although it was slightly inferior to that of PPLC2.

TABLE 2

| Polymer | N/P ratio (+/−) | Residual percent in blood relative to the dosage (%) |
|---|---|---|
| None (naked) | — | 0.13 |
| PPLC2 | 1.5 | 0.44 |
| PPLC2 | 2 | 0.82 |
| PPLC2 | 4 | 3.8 |
| PPLC2 | 6 | 51 |
| PPLC2 | 8 | 57 |
| PPLC2 | 10 | 43 |
| PPLS1 | 6 | 17 |

Figure 9:
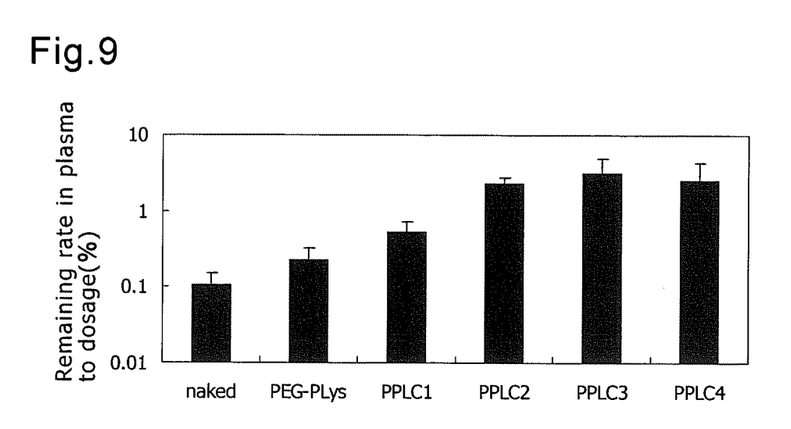
FIG. 9 is a graph showing the result of evaluating blood circulation two hours after the administration of particles prepared using PPLC1 to 4 and PEG-PLys at an N/P ratio of 6 and non-encapsulated (naked) siRNA.

The results of evaluating blood circulation two hours after administration of the particles prepared using PPLC1 to PPLC4 and PEG-PLys at an N/P ratio of 6 and non-encapsulated (naked) siRNA are shown in Table 3 and FIG. 9. Compared with the naked and PEG-PLys, each PPLC exhibited a higher blood-circulating rate. Also, each of PPLC2 to PPLC4 exhibited a higher blood-circulating rate compared with PPLC1.

TABLE 3

| Polymer | N/P ratio (+/−) | Residual percent in blood relative to the dosage (%) |
|---|---|---|
| None (naked) | — | 0.10 |
| PEG-PLys | 6 | 0.23 |
| PPLC1 | 6 | 0.53 |
| PPLC2 | 6 | 2.3 |
| PPLC3 | 6 | 3.1 |
| PPLC4 | 6 | 2.5 |

Figure 10:
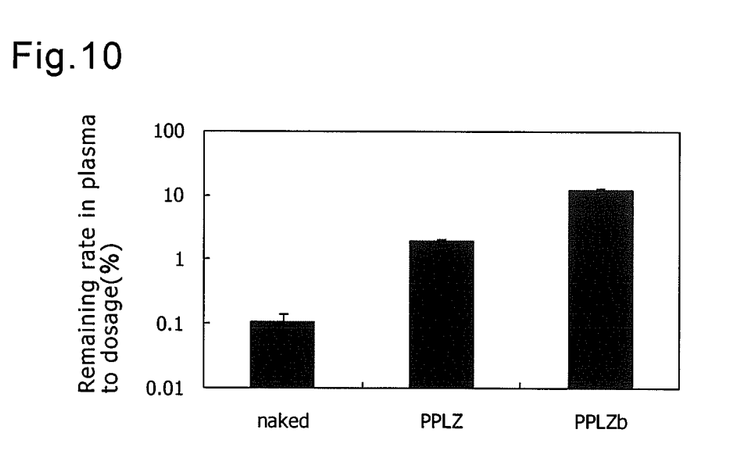
FIG. 10 is a graph showing the result of evaluating blood circulation two hours after the administration of particles prepared using PPLZ at an N/P ratio of 8, particles prepared using PPLZb at an N/P ratio of 8, and non-encapsulated (naked) siRNA.

The results of evaluating blood circulation two hours after administration of the particles prepared using PPLZ and PPLZb at an N/P ratio of 8 and non-encapsulated (naked) siRNA are shown in Table 4 and FIG. 10. PPLZ, in which benzyloxycarbonyl groups were randomly introduced into polylysine units, exhibited an approximately 20-fold higher blood-circulating rate than the naked. On the other hand, PPLZb, which is a triblock polymer, exhibited more than 100-fold higher blood-circulating rate. It is assumed that in the particles prepared using PPLZb, a protective layer made of the hydrophobic polyamino acid chain block was formed inside the shell layer made of polyethylene glycol, and that the siRNA was stably retained further inside thereof.

TABLE 4

| Polymer | N/P ratio (+/−) | Residual percent in blood relative to the dosage (%) |
|---|---|---|
| None (naked) | — | 0.10 |
| PPLZ | 8 | 1.9 |
| PPLZb | 8 | 12.6 |

Figure 11:
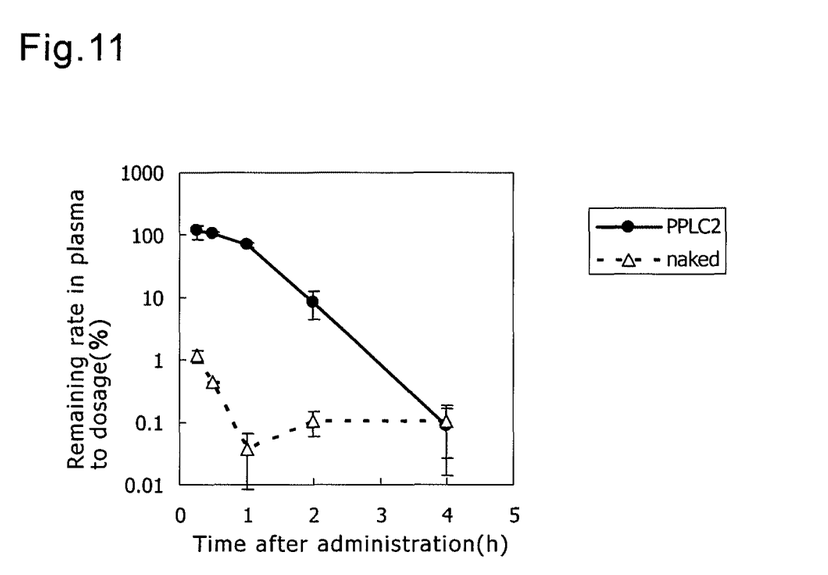
FIG. 11 is a graph showing the result of evaluating blood circulation during the period from 15 minutes to 4 hours after the administration of particles prepared using PPLC2 at an N/P ratio of 6 and non-encapsulated (naked) siRNA.

The results of evaluating blood circulation during the period of 15 minutes to four hours after administration of the particles prepared using PPLC2 at an N/P ratio of 6 and non-encapsulated (naked) siRNA are shown in Table 5 and FIG. 11. The siRNA that was made into particles with PPLC2 exhibited a significantly higher blood-circulating rate than the naked until at least two hours after administration.

TABLE 5

| | Residual percent in blood relative to the dosage (%) | | | | |
|---|---|---|---|---|---|
| Polymer | 15 min later | 30 min later | 1 hour later | 2 hours later | 4 hours later |
| PPLC2 | 115 | 106 | 69 | 8.7 | 0.09 |
| None (naked) | 1.2 | 0.43 | 0.04 | 0.10 | 0.11 |

INDUSTRIAL APPLICABILITY

In addition to the above-mentioned advantages, the block copolymer of the present invention, which contains a hydrophilic polymer chain block and a cationic polyamino acid chain block having a hydrophobic group incorporated into part of the side chain, has another advantage in that it can form stable aggregates with, e.g., siRNA, a small-molecule nucleic acid, which aggregates are in the form of monodisperse particles with an average particle diameter of a few dozen nanomers to a few hundred nanomers, and exhibit long-term circulation in blood as well as high cellular-uptake efficiency. Therefore, the block copolymer is useful as, but not limited to, a carrier to deliver a therapeutic gene into target cells, and can be used in the pharmaceutical and medical industries.

What is claimed is:

1. A block copolymer comprising:
an uncharged hydrophilic polymer chain block selected from a polyethylene glycol block and a polyoxyethylene block; and
a cationic polyamino acid chain block which is a polylysine block, wherein the hydrophilic polymer chain block is covalently bound to one end of the main chain if the polyamino acid chain block and
a hydrophobic group selected from a residue of a sterol derivative and a $C_{12-24}$ hydrocarbyl group, bound to the side chains of not less than 10% and not greater than 70% of the amino acid units in the polyamino acid side chain block via —NH—, —NHCOO—, OR—NHCO—.

2. The block copolymer according to claim 1, represented by general formula I:

or II:

wherein,

A represents a hydrogen atom or a group represented by a formula $R_1(R_2)CH(CH_2)_q$— wherein
  $R_1$ and $R_2$ independently represent a hydrogen atom, a $C_{1-6}$ alkoxy group, an aryloxy group, a cyano group, a carboxyl group, an amino group, a $C_{1-6}$ alkoxycarbonyl group, a $C_{2-7}$ acylamide group, a tri-$C_{1-6}$ alkylsiloxy group, or a silylamino group, or
  $R_1$ and $R_2$ together form an ethylenedioxy or propylenedioxy group, which is unsubstituted or substituted with a $C_{1-3}$ alkyl group, or
  $R_1$ and $R_2$, together with the CH group to which they are attached, form a formyl group,
q represents an integer of 0 to 10, L represents —$(CH_2)_r$NH—, —NHCH$_2$CH$_2$NH—, —NHCH$_2$CH$_2$CH$_2$NH—, or —COCH$_2$CH$_2$—NH— provided that r represents an integer of 0 to 5,
L' represents —CO—, —OCO—$(CH_2)_{r'}$—CO—, or —NHCO—$(CH_2)_{r'}$—CO— provided that r' represents an integer of 1 to 5,
B represents a sterol derivative residue or a $C_{12-24}$ hydrocarbyl group bound via —NH—, —NHCOO—, or —NHCO—,
Q represents NH$_2$, —NHC(=NH)NH$_2$ or a substituent represented by formula IV:

Z represents a hydrogen atom, a $C_{2-12}$ alkylcarbonyl group, a $C_{3-12}$ alkenylcarbonyl group, a $C_{3-12}$ alkenylcarbonyl group, an arylcarbonyl group, an aryloxycarbonyl group, or the same group as defined in B,
Z' represents —NH—$R_3$, provided that $R_3$ is an unsubstituted or substituted, linear or branched $C_{1-12}$ alkyl group,
m is an integer of 55 to 5,000,
n is an integer of 10 to 100,
p is 4,
x is an integer representing the number of units having a substituent Q contained in the polyamino acid chain block, and
y is an integer representing the number of units having a substituent B contained in the polyamino acid chain block, wherein x+y=n, and y accounts for not less than 10% and not greater than 70% of n.

3. The block copolymer according to claim 2, wherein the sterol derivative residue is derived from a compound selected from the group consisting of cholesterol, cholestanol, dihydroxycholesterol, and cholic acid.

4. The block copolymer according to claim 2, wherein the hydrocarbyl group is a $C_{12-20}$ alkyl group.

5. The block copolymer according to claim 2, wherein the hydrocarbyl group is selected from the group consisting of a phenyl, naphthyl and an arylalkyl group comprising phenyl and $C_{1-5}$ alkyl.

6. A complex of a nucleic acid and the block copolymer according to claim 1.

7. The complex according to claim 6, wherein the nucleic acid is selected from the group consisting of oligo- or poly-double stranded RNA, oligo- or poly-double stranded DNA, oligo- or poly-single stranded DNA, and oligo- or poly-single stranded RNA.

8. The complex according to claim 7, wherein the nucleic acid is selected from the group consisting of plasmid DNA, siRNA, micro RNA, antisense nucleic acid, decoy nucleic acid, aptamer, and ribozyme.

9. The complex according to claim 6, which has a core-shell polymeric micelle structure, and encapsulates the nucleic acid in the core part.

10. The complex according to claim 6, which has an N/P ratio of between 1 and 50, wherein the N/P ratio is defined by [the concentration of cation residues in the block copolymer]/[the concentration of the phosphate group in the nucleic acid].

11. The complex according to claim 6, which is in the form of particles having an average particle diameter of from 10 to 300 nm.

\* \* \* \* \*

UNITED STATES PATENT AND TRADEMARK OFFICE
CERTIFICATE OF CORRECTION

| | | |
|---|---|---|
| PATENT NO. | : 8,431,545 B2 | Page 1 of 1 |
| APPLICATION NO. | : 12/922116 | |
| DATED | : April 30, 2013 | |
| INVENTOR(S) | : Kazunori Kataoka et al. | |

It is certified that error appears in the above-identified patent and that said Letters Patent is hereby corrected as shown below:

In the Claims

Column 17, line 26, Claim 1        Delete "main chain if",
                                   Insert --main chain of--

Column 17, line 33, Claim 1        Delete "OR-NHCO-.",
                                   Insert --or -NHCO-.--

Signed and Sealed this
Twenty-eighth Day of January, 2014

Michelle K. Lee
*Deputy Director of the United States Patent and Trademark Office*

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:

```
<223> OTHER INFORMATION: siRNA sense strand

<400> SEQUENCE: 1
cuuacgcuga guacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 2
ucgaaguacu cagcguaagt t                                              21
```